United States Patent
Fehling et al.

(10) Patent No.: US 9,757,111 B2
(45) Date of Patent: Sep. 12, 2017

(54) SURGICAL INSTRUMENT

(71) Applicant: Fehling Instruments Middle East FCZ, Sharjah (AE)

(72) Inventors: Gerald Fehling, Alzenau (DE); Robert Pflugmacher, Berlin (DE)

(73) Assignee: Fehling Instruments Middle East FCZ, Sharjah (AE)

( * ) Notice: Subject to any disclaimer, the term of this patent is extended or adjusted under 35 U.S.C. 154(b) by 364 days.

(21) Appl. No.: 14/421,773

(22) PCT Filed: Aug. 16, 2013

(86) PCT No.: PCT/EP2013/067142
§ 371 (c)(1),
(2) Date: Feb. 13, 2015

(87) PCT Pub. No.: WO2014/027089
PCT Pub. Date: Feb. 20, 2014

(65) Prior Publication Data
US 2015/0230786 A1     Aug. 20, 2015

(30) Foreign Application Priority Data
Aug. 16, 2012   (DE) .................. 10 2012 107 521

(51) Int. Cl.
*A61B 17/58*      (2006.01)
*A61B 17/60*      (2006.01)
(Continued)

(52) U.S. Cl.
CPC ............ *A61B 17/025* (2013.01); *A61B 17/29* (2013.01); *A61B 17/32* (2013.01); *A61B 17/0218* (2013.01);
(Continued)

(58) Field of Classification Search
CPC combination set(s) only.
See application file for complete search history.

(56) References Cited

U.S. PATENT DOCUMENTS 5,720,763 A    2/1998  Tovey
6,582,451 B1   6/2003  Marucci et al.
(Continued)

OTHER PUBLICATIONS

Patent Cooperation Treaty, "International Search Report" issued in International Application No. PCT/EP2013/067142, by European Searching Authority, document of 8 pages, dated Nov. 15, 2013.
(Continued)

*Primary Examiner* — Sameh Boles
(74) *Attorney, Agent, or Firm* — Akerman LLP; Peter A. Chiabotti

(57) ABSTRACT

A surgical instrument with a first contact element and a second contact element for spreading tissue, bone, or the like. The instrument has a stationary base part and a sliding part, which is arranged on the base part in a longitudinally movable manner. The first contact element is integrally molded on the distal end of the base part, and the second contact element is connected to the base part and to the sliding part via a first arm and to the base part via a second arm. The first arm is arranged on the second contact element via a first pivot axis, on the base part via a second pivot axis, and on the sliding part via a third pivot axis, and the second arm is arranged on the second contact element via a fourth pivot axis and on the first contact element via a fifth pivot axis.

12 Claims, 3 Drawing Sheets

(51) Int. Cl.
*A61F 2/00* (2006.01)
*A61B 17/02* (2006.01)
*A61B 17/32* (2006.01)
*A61B 17/29* (2006.01)

(52) U.S. Cl.
CPC ............... *A61B 2017/2926* (2013.01); *A61B 2017/2932* (2013.01); *A61B 2017/2939* (2013.01); *A61B 2017/2944* (2013.01); *A61B 2017/320044* (2013.01)

(56) References Cited

U.S. PATENT DOCUMENTS

| | | |
|---|---|---|
| 7,087,055 B2 | 8/2006 | Lim et al. |
| 7,625,377 B2 | 12/2009 | Veldhuizen et al. |
| 8,523,769 B2 | 9/2013 | Fehling et al. |
| 2003/0187453 A1 | 10/2003 | Schlapfer et al. |
| 2004/0193158 A1 | 9/2004 | Lim et al. |
| 2005/0261683 A1 | 11/2005 | Veldhuizen et al. |
| 2007/0260260 A1 | 11/2007 | Hahn et al. |
| 2008/0234725 A1 | 9/2008 | Griffiths et al. |
| 2009/0012538 A1 | 1/2009 | Saliman et al. |
| 2009/0076607 A1* | 3/2009 | Aalsma ............ A61B 17/8852 623/17.16 |
| 2009/0228025 A1 | 9/2009 | Benson |
| 2011/0237903 A1 | 9/2011 | Fehling et al. |
| 2013/0144388 A1 | 6/2013 | Emery et al. |
| 2014/0296649 A1 | 10/2014 | Fehling et al. |

OTHER PUBLICATIONS

German Patent and Trademark Office, "Office Action," issued in German Patent Application No. 10 2012 107 521.2, by German Examination Office, document of 21 pages, dated May 21, 2013, with an English translation thereof.

* cited by examiner

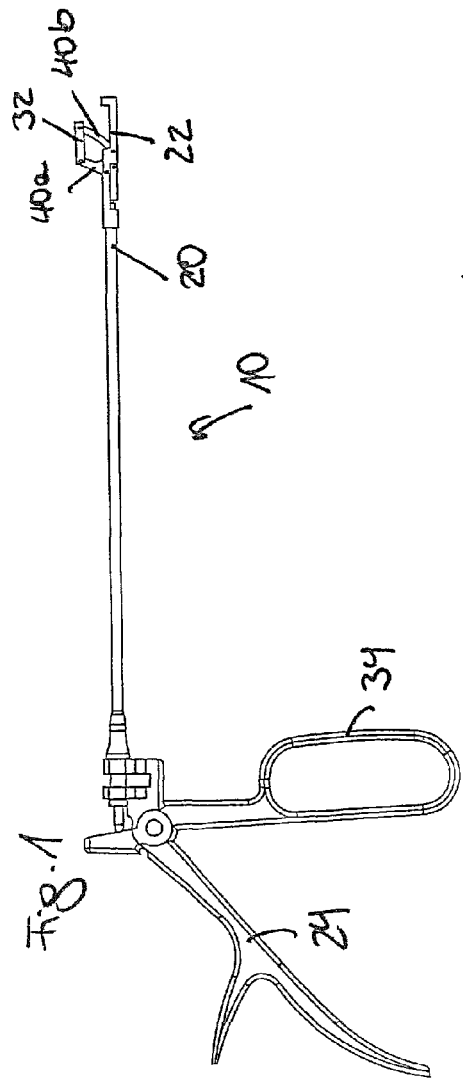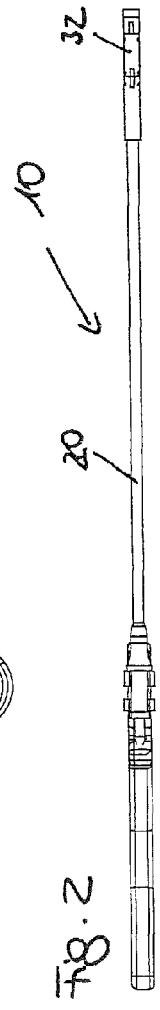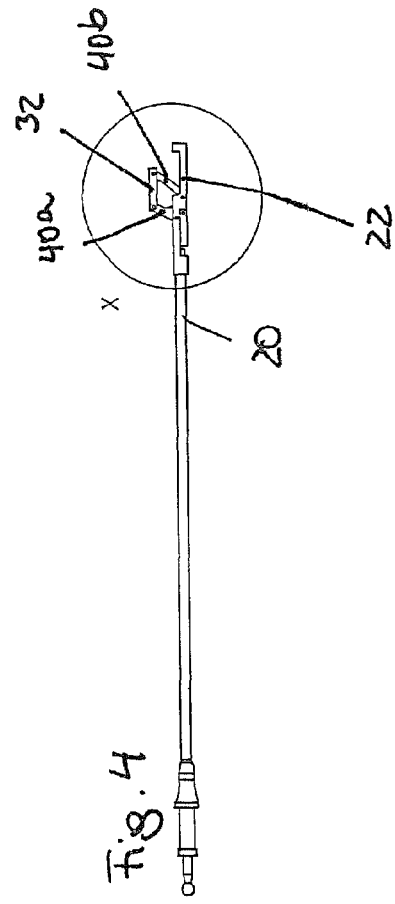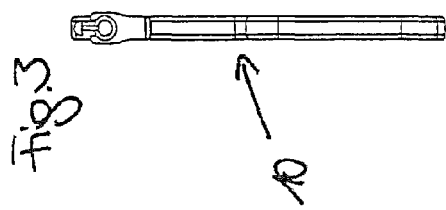

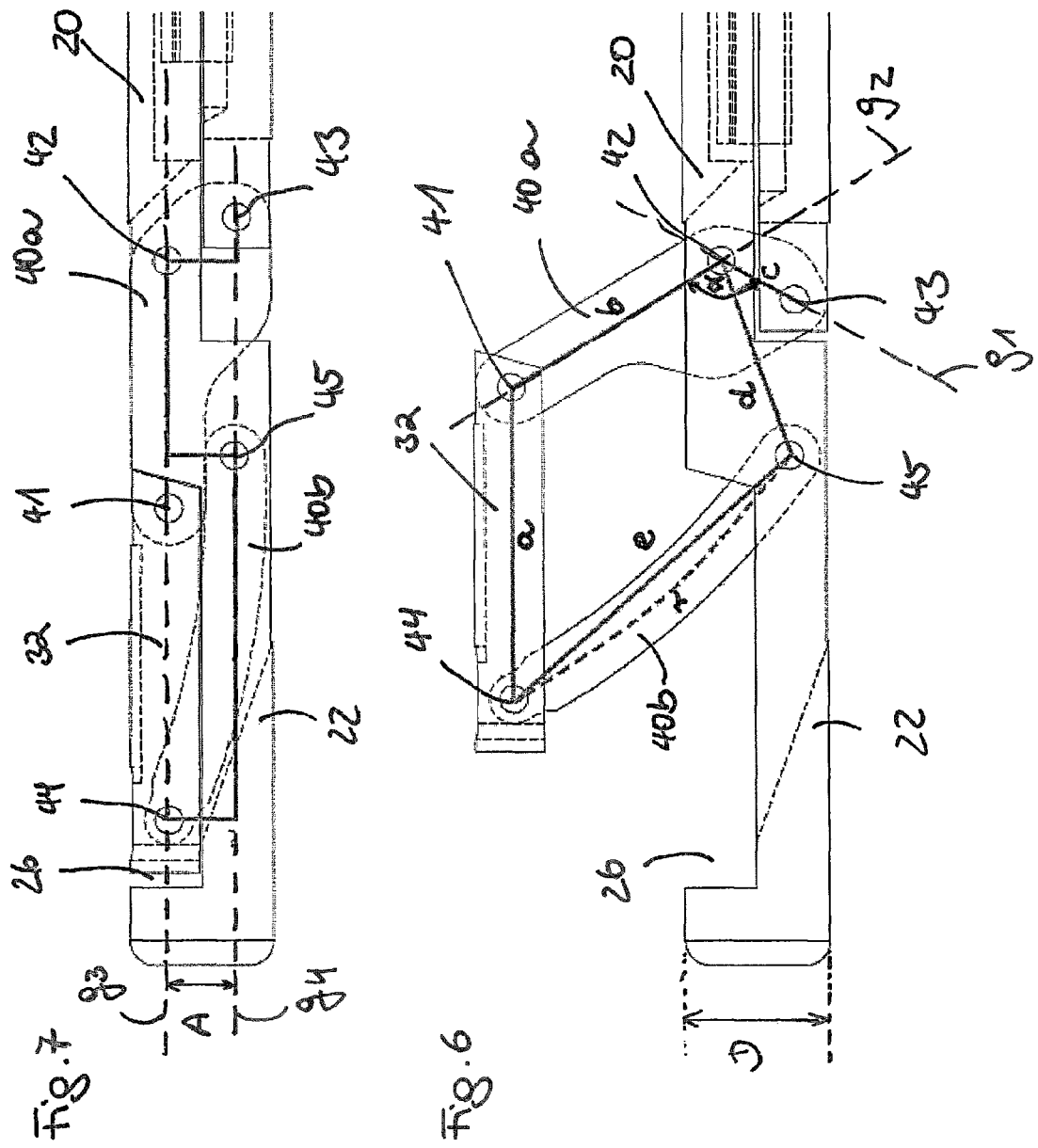

SURGICAL INSTRUMENT

CROSS REFERENCE TO RELATED APPLICATIONS

This application is a §371 National Phase of PCT/EP2013/067142, filed Aug. 16, 2013, which claims priority to German Patent Application No. 10 2012 107 521.2, filed Aug. 16, 2012.

BACKGROUND

The application relates to a surgical instrument according to the features and structures recited herein.

SUMMARY

Surgical instruments for spacing apart tissue elements or spine elements are known, in which two contact elements are spread apart symmetrically to both sides from the center axis of the instrument via a scissors linkage. For example, EP 1 519 685 B1 discloses such an instrument.

The present disclosure provides a surgical instrument for spreading apart tissue, bones, or the like having an alternative design, which enables the surgical instrument to be constructed as very small in particular, in particular for minimally invasive surgery, without substantially impairing the stability at the same time.

The present application provides a surgical instrument having the features and structures recited herein.

Advantageous embodiments and refinements are specified in the further features and structures recited herein.

The surgical instrument has a working end, which has a first and a second contact element for spreading apart tissue, bone, or the like, is distinguished in that the instrument has a stationary base part and a sliding part arranged so it is longitudinally displaceable thereon, wherein the first contact element is arranged integrally on the distal end of the base part, wherein the second contact element is connected via a first arm to the base part and the sliding part and via a second arm to the base part, wherein the first arm is arranged via a first pivot axis on the second contact element, via a second pivot axis on the base part, and via a third pivot axis on the sliding part, and the second arm is arranged via a fourth pivot axis on the second contact element and via a fifth pivot axis on the first contact element of the base part, and wherein the fourth pivot axis is arranged distal from the first pivot axis and the fifth pivot axis is arranged distal from the second pivot axis. It is thus ensured that the arms do not intersect, but rather are arranged adjacent to one another in every position of the second contact element in relation to the first contact element. The first arm acts in particular like a type of rocker or a pivot lever. In particular an alignment of the second contact element in relation to the first contact element is enabled by the first arm, in particular in a stable manner, so that surgical instruments having small dimensions but a high level of effectiveness are possible. In particular, the instrument is distinguished in that the first contact element is arranged integrally on the distal end of the base part and therefore is not moved during the alignment, while only the second contact element is displaced in relation to the base part during the alignment and spreading only occurs in one direction proceeding from the instrument axis of the surgical instrument.

According to one advantageous refinement, the first arm penetrates the base part in a recess in which the second pivot axis is arranged, whereby a more compact structure of the surgical instrument is enabled.

According to one particularly advantageous embodiment, a first straight line which extends perpendicularly through the first pivot axis and perpendicularly through the second pivot axis, intersects a second straight line, which extends perpendicularly through the second pivot axis and perpendicularly through the third pivot axis, in a point, wherein the first and the second straight lines in particular enclose an angle between 90° and 180°. Particularly favorable lever ratios thus result.

One advantageous refinement provides that in a first position of the second contact element, a third straight line intersects both the first pivot axis and also the second pivot axis and the fourth pivot axis perpendicularly and a fourth straight line intersects both the third pivot axis and also the fifth pivot axis perpendicularly and in particular the third straight line and the fourth straight line are arranged in parallel to one another at a spacing A.

One particularly preferred embodiment, provides that the second contact element is displaceable from a first position into a second position, wherein the second contact element is arranged essentially parallel to the first contact element both in the first position and also in the second position. The second contact element is advantageously arranged parallel to the first contact element at least in the first position. In particular, the second contact element is arranged parallel to the first contact element in all positions in relation to the first contact element. Due to the parallel opening, almost no forces act in the direction of the position of the surgical element, so that the surgical element is not displaced during the movement of the working end, which enables more reliable operation.

According to one preferred embodiment, it is provided that the ratio of the spacing between the first pivot axis and the second pivot axis to the spacing between the second pivot axis and the third pivot axis is in the range of 1:2 to 1:5, advantageously in the range of 1:3 to 1:4.

The second contact element is preferably arranged in a recess of the base element in the first position, whereby a more compact structure of the instrument is enabled.

The sliding part is advantageously arranged in the base part, wherein preferably the distal end of the sliding part is accessible through a recess of the base part. On the one hand, the compact structure of the instrument is thus promoted, on the other hand, the recess enables simplified cleaning of the instrument.

According to one advantageous embodiment, the base part is at least sectionally implemented as a tube, in which the sliding part, which is at least sectionally implemented as a rod, is arranged, which further promotes the compact structure of the instrument.

The surgical element is particularly preferably implemented as a tube shaft instrument.

BRIEF DESCRIPTION OF THE DRAWINGS

The features and structures of the present disclosure will be explained in detail on the basis of the following figures. In the figures:

FIG. 1 shows a side view of an exemplary embodiment of a surgical instrument according to the present disclosure, FIG. 2 shows a top view of the surgical instrument according to FIG. 1, FIG. 3 shows a frontal view of the surgical instrument according to FIG. 1, FIG. 4 shows the surgical instrument according to FIG. 1 without the handle elements, FIG. 6 shows an x-ray view of the detail enlargement according to FIG. 5 having the second contact element in a second position, and FIG. 7 shows the x-ray view according to FIG. 6 having the second contact element in the first position.

DETAILED DESCRIPTION OF THE ILLUSTRATED EMBODIMENTS

Figure 5:
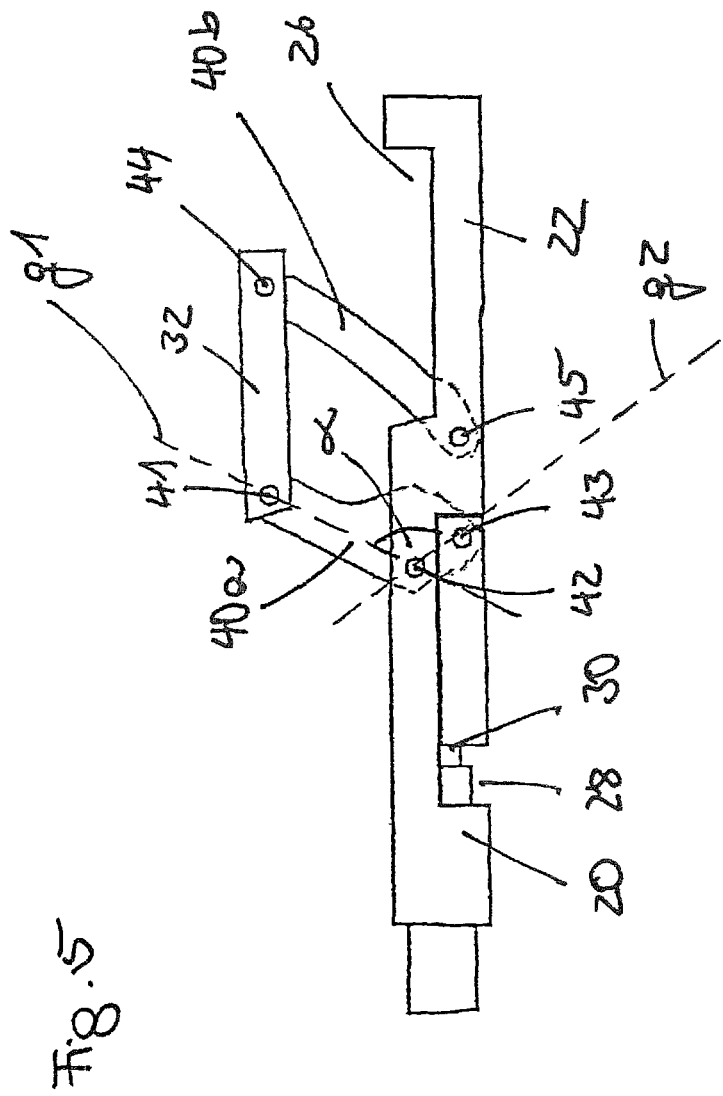
FIG. 5 shows a detail enlargement from FIG. 4.

FIGS. 1 to 7 show various views of a surgical instrument 10, wherein all reference signs are not specified in all figures for better comprehensibility.

The surgical instrument 10 has a stationary base part 20, which is implemented in particular at least sectionally as a tube, and a sliding part 30 arranged so it is longitudinally displaceable thereon, which is in particular arranged at least sectionally as a rod and in particular is arranged so it is longitudinally displaceable coaxially in the base part 20. The stationary base part 20 is preferably detachably connected to a first handle part 24, while the second sliding part 30 is also preferably detachably connected to a second handle part 34. By pivoting the two handle parts 24, 34 in relation to one another, the longitudinal displacement of the sliding part 30 in relation to the base part 20 is achieved. In particular, the surgical instrument 10 is implemented in this case as a tube shaft instrument.

A first contact element 22 is integrally arranged on the distal end of the base part 20. The distal end of the sliding part 30 is connected to a second contact element 32 via a first arm 40a. The second contact element 32 is furthermore connected to the base part 20, in particular the first contact element 22 of the base part 20, via a second arm 40b. The first arm 40a is connected so it is rotatably mounted on the second contact element 32 via a first pivot axis 41, while the second contact element 32 is connected so it is rotatably mounted to the distal end of the sliding part 30 via a third pivot axis 43. The first arm 40a is furthermore arranged so it is pivotably mounted via a second pivot axis 42 on the base part 20. The second arm 40b is arranged so it is rotatably mounted via a fourth pivot axis 44 on the second contact element 32, while the second arm 40b is arranged so it is rotatably mounted on the base part 20 via a fifth pivot axis 45. The pivot axes 41, 42, 43, 44, 45 are each arranged in parallel to one another and extend in particular perpendicularly to the longitudinal axis of the surgical instrument 10, in particular to the longitudinal axis of the tubular base part 20 or the rod-shaped sliding part 30. In the illustrations of FIGS. 5, 6, and 7, the pivot axes 41, 42, 43, 44, and 45 extend perpendicularly to the plane of the paper.

The fourth pivot axis 44 is arranged distal from the first pivot axis 41, while the fifth pivot axis 45 is arranged distal from the second pivot axis 42. The two arms 40a, 40b thus lie adjacent to one another and do not intersect.

The second pivot axis 42 forms the rotational axis, about which the first arm 40a is rotated in relation to the base part 20 upon longitudinal displacement of the sliding part 30.

The first pivot axis 41 and the second pivot axis 42 lie on a first straight line g1, while the third pivot axis 43 and the second pivot axis 42 lie on a second straight line g2. In this case, the first straight line g1 intersects the first pivot axis 41 and the second pivot axis 42 perpendicularly, while the second straight line g2 intersects the third pivot axis 43 and the second pivot axis 42 perpendicularly. In one embodiment, the first straight line g1 and the second straight line g2 are not coincident, but rather they intersect at a point, specifically in particular at the second pivot axis 42, and enclose an angle α therein, which is in particular between 90° and 180°, for example, between 120° and 135°, in particular 121.33° or 133.03°.

The first pivot axis 41, the second pivot axis 42, and the third pivot axis 43 are all arranged on the first arm 40a and are fixed in relation to one another. The angle α is therefore not variable for a given instrument 10.

If the sliding part 30 is displaced in the distal direction in the base part 20, the arm 40a pivots about the second pivot axis 42, wherein the first pivot axis 41 is moved away from the base part 20 and the second contact element 32 also moves in this case. As shown in FIGS. 1 to 6, the second contact element 32 is finally located in an aligned second position, in which it is arranged parallel to the first contact element 22. If the sliding part 30 is drawn in the proximal direction, the arm 40a pivots back about the second pivot axis 42 and moves the first contact element 22 into a first position (cf. FIG. 7), in which it presses against the base part 20 and in particular comes to rest in a recess 26 of the base part 20. The first position is in particular the closed position of the instrument 10. The second contact element 32 is also arranged parallel to the first contact element 22 in this first position and in particular in all intermediate positions. The second contact element 32 is dimensioned in particular such that it does not substantially enlarge the external dimensions of the base part 20 when it is in contact with the base part 20, in particular in the recess 26.

As is recognizable in FIG. 7, the first pivot axis 41, the second pivot axis 42, and the fourth pivot axis 44 lie in one plane in the first position of the second contact element 32 or, in other words, a third straight line g3 intersects both the first pivot axis 41 and also the second event axis 42 and the fourth pivot axis 44 perpendicularly. In particular, the third straight line g3 lies parallel to a fourth straight line g4, which perpendicularly intersects the third pivot axis 43 and the fifth pivot axis 45, in the first position of the second contact element 32. In this case, the third straight line g3 and the fourth straight line g4 have a spacing A to one another, which, in the case of an external diameter D of the instrument 10, can be between 20% and 60%, in particular approximately 30% to 50%, of the external diameter D.

During the movement of the second contact element 32 in relation to the first contact element 22 and the base part 20, the second arm 40b is pivoted about the fifth pivot axis 45. The second arm 40b is essentially used to support the distal end of the second contact element 32 in relation to the base part 20, in particular the first contact element 22 of the base part 20.

The second part 40b can be implemented as curved and in particular can be part of an external circumference of a circle having a radius r.

The distal end of the sliding part 30 can be arranged inside the base part 20. It is preferably externally accessible through a recess 28, to enable better cleaning.

The first arm 40a penetrates the base part 20 in a recess in which the second pivot axis 42 is arranged, in particular in this manner to enable the arrangement of the first pivot axis 41 and the third pivot axis 43 essentially on two different sides of the second pivot axis 42.

The first pivot axis 41 and the fourth pivot axis 44, which are both arranged on the second contact element 32, have a spacing a. The first pivot axis 41 and the second pivot axis 42, which are both arranged on the first arm 40a, have a spacing b. The second pivot axis 42 and the fifth pivot axis 4, which are both arranged on the base part 20, have a spacing d. The fourth pivot axis 44 and the fifth pivot axis 45, which are both arranged on the second arm 40b, have a spacing e. The second pivot axis 42 and the third pivot axis 43, which are both arranged on the first arm 40a, have a spacing c to one another. The ratio of c:b is in the range of 1:2 to 1:5, in particular in the range of 1:3 to 1:4.

LIST OF REFERENCE SIGNS 10 instrument
20 base part
22 first contact element
24 first handle part
26 recess
28 recess
30 sliding part
32 second contact element
34 second handle part
40a first arm
40b second arm
41 first pivot axis
42 second pivot axis
43 third pivot axis
44 fourth pivot axis
45 fifth pivot axis
g1 first straight line
g2 second straight line
g3 third straight line
g4 fourth straight line
α angle
a spacing
b spacing
c spacing
d spacing
e spacing
A spacing
D diameter
r radius

The invention claimed is:

1. A surgical instrument, comprising: a stationary base part terminating to a working end, which has a first contact element and a second contact element for spreading apart tissue, bone, or the like; a sliding part arranged longitudinally displaceable on the stationary base part, wherein the first contact element is arranged integrally on a distal end of the stationary base part, wherein the second contact element is connected via a first arm to the stationary base part and the sliding part and via a second arm to the stationary base part, wherein the first arm is arranged via a first pivot axis on the second contact element, via a second pivot axis on the stationary base part, and via a third pivot axis on the sliding part, and the second arm is arranged via a fourth pivot axis on the second contact element and via a fifth pivot axis on the first contact element, wherein the fourth pivot axis is arranged distal from the first pivot axis and the fifth pivot axis is arranged distal from the second pivot axis, and wherein the second contact element is arranged in a first position in a recess of the base part.

2. The surgical instrument according to claim 1, wherein the first arm penetrates the stationary base part in a recess, in which the second pivot axis is arranged.

3. The surgical instrument according to claim 1, wherein a first straight line perpendicularly through the first pivot axis and the second pivot axis, and a second straight line perpendicularly through the second pivot axis and the third pivot axis intersect in a point, and the two straight lines enclose an angle (α) between approximately 90° and 180°.

4. The surgical instrument according to claim 1, wherein in a first position of the second contact element, a third straight line perpendicularly intersects both the first pivot axis and also the second pivot axis and the fourth pivot axis and a fourth straight line (g4) perpendicularly intersects both the third pivot axis and also the fifth pivot axis, and the third straight line and the fourth straight line are arranged parallel to one another at a spacing.

5. The surgical instrument according to claim 1, wherein the second contact element is displaceable from a first position into a second position, wherein the second contact element is arranged approximately parallel to the first contact element both in the first position and also in the second position.

6. The surgical instrument according to claim 1, wherein a ratio of a first spacing between the first pivot axis and the second pivot axis to a second spacing between the first pivot axis and the third pivot axis is in the range of approximately 1:2 to 1:5.

7. The surgical instrument according to claim 1, wherein the sliding part is arranged in the stationary base part, wherein a distal end of the sliding part is accessible through a recess of the stationary base part.

8. The surgical instrument according to claim 1, wherein the stationary base part is at least sectionally implemented as a tube, in which the sliding part, which is at least sectionally implemented as a rod, is arranged so it is longitudinally displaceable.

9. The surgical instrument according to claim 1, wherein the surgical instrument is implemented as a tube shaft instrument.

10. A surgical instrument, comprising: an elongated stationary base part with a work end; a sliding part arranged longitudinally displaceable on the stationary base part; a first spreading element located at the work end; a second spreading element connected to the stationary base part and the sliding part via a first arm, the second spreading element also connected to the sliding part via a second arm; wherein the first arm is arranged via a first pivot axis on the second spreading element, via a second pivot axis on the stationary base part, and via a third pivot axis on the sliding part, wherein the second arm is arranged via a fourth pivot axis on the second spreading element and via a fifth pivot axis on the first spreading element, wherein the fourth pivot axis is arranged distal from the first pivot axis and the fifth pivot axis is arranged distal from the second pivot axis, and wherein the second spreading element is arranged in a first position in a recess of the base part.

11. The surgical instrument according to claim 10, wherein the first arm penetrates the stationary base part in a recess, in which the second pivot axis is arranged.

12. The surgical instrument according to claim 10, wherein the second spreading element is displaceable from a first position into a second position, wherein the second spreading element is arranged approximately parallel to the first contact element both in the first position and also in the second position.

* * * * *